(12) United States Patent
Kalvin

(10) Patent No.: US 9,858,716 B2
(45) Date of Patent: Jan. 2, 2018

(54) FAST THREE-DIMENSIONAL VISUALIZATION OF OBJECT VOLUMES WITHOUT IMAGE RECONSTRUCTION BY DIRECT DISPLAY OF ACQUIRED SENSOR DATA

(75) Inventor: Alan D. Kalvin, Irvington, NY (US)

(73) Assignee: International Business Machines Corporation, Armonk, NY (US)

(*) Notice: Subject to any disclaimer, the term of this patent is extended or adjusted under 35 U.S.C. 154(b) by 1108 days.

(21) Appl. No.: 12/038,862

(22) Filed: Feb. 28, 2008

(65) Prior Publication Data

US 2009/0219289 A1    Sep. 3, 2009

(51) Int. Cl.
| | |
|---|---|
| *G06T 15/30* | (2011.01) |
| *G06T 19/00* | (2011.01) |
| *A61B 6/03* | (2006.01) |
| *A61B 6/00* | (2006.01) |
| *G06T 17/00* | (2006.01) |
| *G06T 15/10* | (2011.01) |
| *G06T 15/20* | (2011.01) |
| *G06F 3/0481* | (2013.01) |

(52) U.S. Cl.
CPC ............ *G06T 19/00* (2013.01); *A61B 6/037* (2013.01); *A61B 6/466* (2013.01); *G06F 3/04815* (2013.01); *G06T 15/10* (2013.01); *G06T 15/20* (2013.01); *G06T 17/00* (2013.01); *G06T 2219/008* (2013.01)

(58) Field of Classification Search
CPC ......... A61B 6/482; A61B 6/504; A61B 6/527; A61B 6/5288; A61B 5/7207; A61B 6/481; A61B 6/503; A61B 6/541; A61B 5/055; A61B 5/7285; A61B 6/03; G06T 7/00; G06T 15/20; G06T 19/00; G06T 15/10; G06T 17/00; G01R 3/4824; G06F 3/04815

USPC ............... 345/418, 156; 703/1, 6, 13, 23; 600/300; 707/600, 609; 324/300, 323; 3/418, 156

See application file for complete search history.

(56) References Cited

U.S. PATENT DOCUMENTS 5,257,183 A * 10/1993 Tam ..................... G06T 11/005
  378/4
5,333,164 A * 7/1994 Tam ................................ 378/8
(Continued)

OTHER PUBLICATIONS

Brenner, DJ et al. "Estimated Risks of Radiation-Induced Fatal Cancer from Pediatric CT." AJR vol. 176, pp. 289-296, Feb. 2001.
Elvins, Todd. "Introduction to Volume Visualization: Imaging Multi-dimensional Scientific Data." SIGGRAPH 94, Course #10 Notes, Jul. 25, 1994.
FDA Public Health Notification. "Reducing Radiation Risk from Computed Tomography for Pediatric and . . . " Rockville, MD: Food and Drug Administration, Nov. 2, 2001.
(Continued)

*Primary Examiner* — Abderrahim Merouan
(74) *Attorney, Agent, or Firm* — Steven M. Greenberg, Esq.; CRGO Law

(57) ABSTRACT

Embodiments of the present invention address deficiencies of the art in respect to 3D visualization of object volumes and provide a method, system and computer program product for fast 3D visualization of object volumes without image reconstruction by direct display of acquired sensor data. In an embodiment of the invention, a method for fast 3D visualization of object volumes without image reconstruction can be provided. The method can include acquiring a 3D dataset from an scanner of a 3D object volume, slicing the acquired sensor data without image reconstruction to produce a sequence of 2D images in Radon space and playing back the sequence of 2D images in a movie player to provide a rotating view of the 3D object volume.

26 Claims, 1 Drawing Sheet

(56) References Cited

U.S. PATENT DOCUMENTS

| | | | |
|---|---|---|---|
| 5,365,560 A * | 11/1994 | Tam | G06T 11/005 378/14 |
| 5,420,788 A * | 5/1995 | Vissers | 378/10 |
| 5,465,283 A * | 11/1995 | Tam | 378/4 |
| 5,500,883 A * | 3/1996 | Hsiao et al. | 378/4 |
| 5,603,322 A * | 2/1997 | Jesmanowicz et al. | 600/410 |
| 5,901,195 A * | 5/1999 | Sauer | G06T 11/006 378/4 |
| 6,023,495 A * | 2/2000 | Adler | A61B 6/032 378/4 |
| 6,298,110 B1 * | 10/2001 | Ning | 378/4 |
| 6,763,081 B2 * | 7/2004 | Tam | 378/4 |
| 6,954,067 B2 * | 10/2005 | Mistretta | G01R 33/56308 324/307 |
| 6,990,167 B2 * | 1/2006 | Chen | 378/4 |
| 7,020,318 B2 | 3/2006 | Oshio | |
| 7,218,702 B2 * | 5/2007 | Mistretta et al. | 378/21 |
| 7,394,887 B2 * | 7/2008 | Hsieh | A61B 6/4447 378/17 |
| 7,583,992 B2 * | 9/2009 | Mistretta et al. | 600/420 |
| 7,647,088 B2 * | 1/2010 | Mistretta et al. | 600/428 |
| 8,219,176 B2 * | 7/2012 | Doyle | G01R 33/482 382/128 |
| 8,472,688 B2 * | 6/2013 | Samsonov et al. | 382/130 |
| 2004/0066876 A1 * | 4/2004 | Tam | A61B 6/032 378/4 |
| 2004/0240604 A1 * | 12/2004 | Wang | G01N 23/046 378/19 |
| 2005/0033158 A1 * | 2/2005 | Vu | 600/416 |
| 2006/0079754 A1 * | 4/2006 | Welch et al. | 600/410 |
| 2007/0010731 A1 * | 1/2007 | Mistretta | 600/407 |
| 2007/0156044 A1 * | 7/2007 | Mistretta | A61B 5/055 600/410 |
| 2007/0167707 A1 * | 7/2007 | Mistretta et al. | 600/407 |

OTHER PUBLICATIONS

Fratt, Lisa. "3D Rendering Across the Enterprise." Health Imaging & IT, Special Section on Advanced Visualization, Apr. 1, 2007.

Frush, DP et al. "Computed Tomography and Radiation Risks: What Pediatric Health Care Providers Should Know." Pediatrics112, pp. 951-957, 2003.

Grevera, GL and JK Udupa. "GIMP—Generalized Maximum Intensity Projection." Proc. SPIE Medical Imaging Conf. vol. 5367, 2004.

Gottfried, KD and G Penn. "Radiation in Medicine . . . " Committee for Review and Evaluation of . . . the Nuclear Regulatory Commission, Institute of Medicine, 1996.

IBM Academy of Technology Study. "Enabling Technologies for Information Based Medicine." 2005.

Jan, J. "Medical Image Processing, Reconstruction and Restoration: Concepts and Methods." CRC Press, 2006.

Kaufman, A. "Volume Visualization." IEEE Computer Society Press, 1991.

Manssour, IH et al. "High Performance Approach for Inner Structures Visualisation in Medical Data." Int. J. Computer Applications and Technology, vol. 22, No. 1, 2005.

Mora, B and DS Elbert. "Low-Complexity Maximum Intensity Projection." ACM Trans. Graphics, 24(6), pp. 1392-1416, 2005.

NCI Newsletter. "Radiation and Pediatric Computed Tomography: A Guide for Health Professionals." National Cancer Institute, Summer 2002.

Neophytou, Neophytos et al. "Hardware acceleration vs. algorithmic acceleration: Can GPU-based processing beat complexity . . . ?" Proc. SPIE Medical Imaging Conf, 2007.

Sakamoto, Masaharu et al. "An Implementation of the Feldkamp Algorithm for Medical Imaging on Cell." http://www.gspx.com, GSPx 2005, 2005.

Slovis, TL. "Children, Computed Tomography Radiation Dose, and the as Low as Reasonably Achievable (ALARA) Concept." Pediatrics 112, pp. 971-972, 2003.

Manssour, et al., "High Performance Approach for Inner Structures . . . ," INCCA, vol. 22, No. 1, 2005.

* cited by examiner

FAST THREE-DIMENSIONAL VISUALIZATION OF OBJECT VOLUMES WITHOUT IMAGE RECONSTRUCTION BY DIRECT DISPLAY OF ACQUIRED SENSOR DATA

BACKGROUND OF THE INVENTION

Field of the Invention

The present invention relates to the field of computer imaging and more particularly to three-dimensional visualization of object volumes.

Description of the Related Art

Computer imaging, synonymously referred to as digital imaging, is a field of computer science relating to the acquisition and manipulation of digital imagery. In the study and practice of computer imaging, images can be acquired either directly (being the data acquired from one or more sensors), or acquired indirectly (being produced through a computed transformation of the acquired sensor data), and stored digitally in memory. The images can be stored in raster form as bitmapped graphics, or in vector form through one or more representative expressions. Once stored, images can be manipulated to enhance the images or to derive new images. Computer imaging generally encompasses a wide field of application ranging from design and computer graphics, to medical systems, to machine vision. Computer imaging has particular application to medical imaging though other emerging fields include imaging of cargo and vehicles for homeland security.

Three-dimensional (3D) visualization is a part of computer imaging the refers to the rendering of real world 3D objects into some form of computerized 3D representation, whether it be projected on a two-dimensional (2D) computer screen, or viewed through immersive virtual reality equipment. Volume visualization is a form of 3D visualization where physical objects modeled in 3D can be studied and examined in greater detail and the modeled objects further can be manipulated in order to, for example, provide visual confirmation of the content of a visualized volume, test scientific hypotheses in relation to a visualized volume, to simulate a process relating to the visualized volume, or to practice a medical procedure on a portion of the visualized volume. Current applications of this type include medical imaging, surgical teaching and planning, geophysical sensing, homeland security and weather modeling.

Volume visualization is widely-used in biomedical imaging for displaying of 3D volumetric images of object volumes. In the case of tomographic imaging including positron emission tomography (PET) scanning, computed axial tomography (CT) and X-ray tomography, and also Magnetic Resonance Imaging (MRI), volume visualization is used in applications such as cancer diagnosis, magnetic resonance angiography imaging (MRA) and other cardiac and neurological vasculature imaging, the evaluation of breast implant morphology, and magnetic resonance cholangiopancreatography. Currently, the time-consuming, computationally intensive processing that is required for MRI and tomographic volumetric visualization severely limits its practical and clinical application. In addition, the problem is exacerbated by the growing size of MRI and tomographic images, resulting from on-going improvements in the resolution of MRI and tomographic scanners.

For volume visualization on standard 2D computer displays, two major imaging techniques include Maximum Intensity Projection (MIP) and Volume Rendering (VR). The three basic steps common to both techniques include first the reconstruction of images from acquired sensor data, second the computation of a set of 2D projections of the 3D sensor data, and third a graphical display of a "movie", where each frame is a 2D projection image, giving the viewer the perception of a rotating 3D object on the 2D screen. In as much as the images acquired from sensor data must be reconstructed, both methods are known to be computationally expensive. Furthermore, as both methods are lossy in nature, the addition of image reconstruction noise cannot be avoided, resulting in low quality 2D projection images, which in turn result in low quality visualizations.

BRIEF SUMMARY OF THE INVENTION

Embodiments of the present invention address deficiencies of the art in respect to 3D visualization of object volumes and provide a novel and non-obvious method, system and computer program product for fast 3D visualization of object volumes without image reconstruction by direct display of acquired sensor data. In an embodiment of the invention, a method for fast 3D visualization of object volumes without image reconstruction can be provided. The method can include acquiring a 3D dataset from an scanner of a 3D object volume, slicing the acquired 3D dataset without image reconstruction to produce a sequence of 2D images in Radon space, and playing back the sequence of 2D images in a movie player to provide a dynamic depiction of a rotating view of the 3D object volume.

In one aspect of the embodiment, the 3D dataset acquired by scanning a 3D object can include a 3D dataset acquired by Single Photon Emission Computed Tomography (SPECT), an Optical coherence tomography (OCT), an Electrical Impedance Tomography (EIT), an Electrical Resistivity Tomography (ERT), an Electrical Capacitance tomography (ECT), Cryo-electron Tomography (Cryo-ET), Magnetic Induction Tomography (MIT), Optical Projection Tomography (OPT), or Ultrasound assisted optical tomography (UAOT). Finally, in yet another aspect of the embodiment, playing back the sequence of 2D images in a movie player to provide a rotating view of the 3D object volume, can include playing back the sequence of 2D images in a movie player to provide a rotating view of the 3D object volume as a preview to a medical imaging scan prior to reconstructing the 3D dataset.

In an alternative embodiment, the 3D dataset acquired is 3D "k-space data" (or Fourier Space data) from an MRI scanner, which is then converted into 3D projection data. This process of converting k-space data into projection data is achieved by using the standard technique used for "projection based" reconstruction of MRI for converting Fourier Space into Projection Space, as described in U.S. Pat. No. 5,243,284 to Noll, the entire teachings of which are incorporated by reference. Finally, in yet another aspect of the embodiment, playing back the sequence of 2D images in a movie player to provide a rotating view of the 3D object volume, can include playing back the sequence of 2D images in a movie player to provide a rotating view of the 3D object volume as a preview to a medical imaging scan prior to reconstructing the 3D dataset.

In another embodiment of the invention, an imaging data processing system can be provided. The system can include a scanner, an data acquisition module coupled to the scanner and configured to acquire an image of 3D volumetric sensor data for an object volume from the scanner, data conversion logic coupled to the data acquisition module, the logic including program code enabled to convert the acquired data into a stack of 2D slices in Radon coordinate space without first reconstructing the image, and a movie player configured to play back the stack of 2D slices as a rotating view of the object volume. For example, the scanner can be a tomographic scanner or an MRI scanner. Optionally, the object volume can be either a package or luggage.

Additional aspects of the invention will be set forth in part in the description which follows, and in part will be obvious from the description, or may be learned by practice of the invention. The aspects of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE SEVERAL VIEWS OF THE DRAWINGS

The accompanying drawings, which are incorporated in and constitute part of this specification, illustrate embodiments of the invention and together with the description, serve to explain the principles of the invention. The embodiments illustrated herein are presently preferred, it being understood, however, that the invention is not limited to the precise arrangements and instrumentalities shown, wherein.

DETAILED DESCRIPTION OF THE INVENTION

Embodiments of the present invention provide a method, system and computer program product for fast 3D visualization of object volumes without image reconstruction by direct display of acquired sensor data. In accordance with an embodiment of the present invention, an image of 3D volumetric data for an object volume can be acquired through volumetric scanning, for instance tomographic or MRI scanning. 2D slices of the 3D volumetric data can be acquired by converting the 3D volumetric data into Radon space. Thereafter, the 2D slices can be presented sequentially in a movie player to simulate a 3D rotating view of the object volume without having first reconstructed the image.

Figure 1:
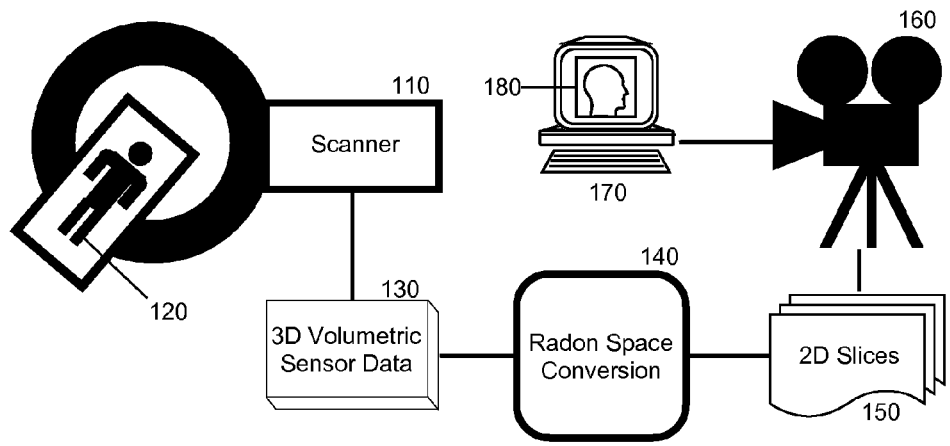
FIG. 1 is a block diagram illustrating a process for fast 3D visualization of object volumes without image reconstruction by direct display of acquired sensor data.

In further illustration, FIG. 1 is a block diagram illustrating a process for fast 3D visualization of object volumes without image reconstruction by direct display of acquired sensor data. Initially, a 3D volumetric dataset 130 can be acquired in respect to an object volume 120 through a volumetric scanner 110. Exemplary forms of the scanner 110 can include a tomographic scanner, CT scanner, x-ray scanner, PET scanner, MRI scanner, etc. Once acquired, the 3D volumetric sensor data 130 can be subjected to Radon space conversion 140 in order to produce a series of 2D slices 150. Finally, the 2D slices 150 can be rendered as frames in a movie by movie player 160 and displayed as a rotating view 180 in computer workstation 170.

Figure 2:
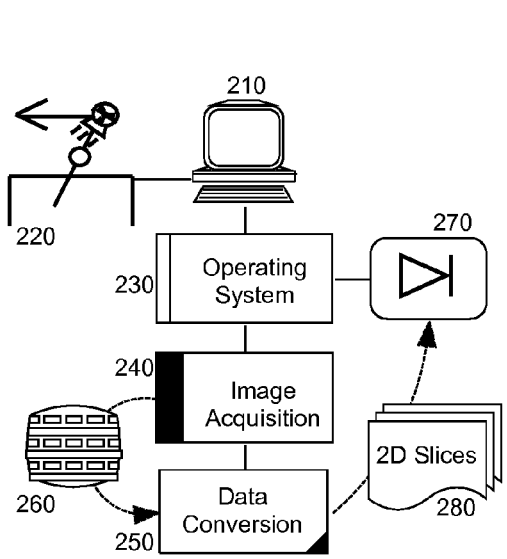
FIG. 2 is a schematic illustration of a computer imaging data processing system configured for fast 3D visualization of object volumes without image reconstruction by direct display of acquired sensor data; and, FIG. 3 is a flow chart illustrating a process for fast 3D visualization of object volumes without image reconstruction by direct display of acquired sensor data.

The process described herein can be implemented in a computer imaging data processing system. In illustration, FIG. 2 schematically depicts a computer imaging data processing system configured for fast 3D visualization of object volumes without image reconstruction by direct display of acquired sensor data. The system can include a host computing platform 210 coupled to a 3D scanner 220. The 3D scanner 220 can include by way of example, a tomographic scanner, CT scanner, x-ray scanner, PET scanner, MRI scanner, and the like.

The host computing platform 210 can support the operation of operating system 230 which in turn can host data acquisition module 240 and movie player 270. The image acquisition module 240 can be configured to acquire a 3D volumetric dataset 260 from the scanner 220. Data conversion logic 250 can be coupled to the data acquisition module and can include program code enabled to convert the 3D data 260 directly into a stack of 2D slices 280 in Radon coordinate space without first reconstructing the image 260. Thereafter, the movie player 270 can play back the stack of 2D slices 280 to provide a rotating view of the object volume through a display in the host computing platform 210.

Figure 3:
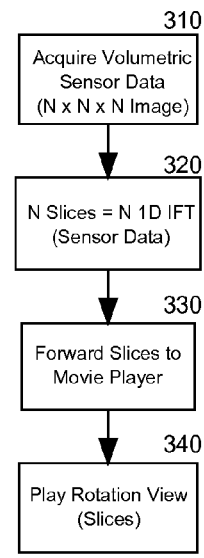

In yet further illustration, FIG. 3 is a flow chart illustrating a process for fast 3D visualization of object volumes without image reconstruction by direct display of acquired sensor data. Beginning in block 310, volumetric sensor data can be acquired for an N×N×N image of an object volume. In the case of x-ray CT, the volumetric dataset is acquired in Radon Space representation. In the case of MRI, the dataset is acquired in K-Space representation, and is subsequently transform into Radon Space representation by applying N one-dimensional inverse Fourier transforms of the N×N×N K-Space dataset to transform the dataset into the Radon coordinate space. (The specific details of this K-Space to Radon Space transformation process in described in U.S. Pat. No. 5,243,284 to Noll). The 3D dataset in Radon Space in then converted into a set of 2D slices. Specifically, the N×N×N image having Radon coordinate dimensions of distance and angle $\Theta$ (Radon coordinates) and axial plane position, can be sliced along the $\Theta$ dimension to produce a stack of 2D slices expressed by the Radon space and the axial plane position dimensions. Thereafter, in block 330 the 2D slices can be forwarded as a sequence of frames to a movie player for playback, and in block 340 a rotation view of the slices can be presented.

Notably, according to the process of FIG. 3, the reconstruction of the image of the object volume can be avoided along with both the computational expense and the resultant image quality degradation. As such, tomographic imaging can be applied to applications requiring high speed imaging, including package and baggage inspection in the context of homeland security. Additionally, MRI and tomographic imaging can enjoy an image preview feature to view 3D data before image reconstruction. Thus, quality control in data acquisition can be provided by detecting poor quality scan data, e.g. with motion artifacts, before image reconstruction, providing a way to avoid the unnecessary time and expense of reconstructing unusable data.

Embodiments of the invention can take the form of an entirely hardware embodiment, an entirely software embodiment or an embodiment containing both hardware and software elements. In a preferred embodiment, the invention is implemented in software, which includes but is not limited to firmware, resident software, microcode, and the like. Furthermore, the invention can take the form of a computer program product accessible from a computer-usable or computer-readable medium providing program code for use by or in connection with a computer or any instruction execution system.

For the purposes of this description, a computer-usable or computer readable medium can be any apparatus that can contain, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution. Input/output or I/O devices (including but not limited to keyboards, displays, pointing devices, etc.) can be coupled to the system either directly or through intervening I/O controllers. Network adapters may also be coupled to the system to enable the data processing system to become coupled to other data processing systems or remote printers or storage devices through intervening private or public networks. Modems, cable modem and Ethernet cards are just a few of the currently available types of network adapters.

I claim:

1. A method for fast three-dimensional (3D) visualization of object volumes without image reconstruction, the method comprising:
    acquiring a volumetric sensor 3D dataset from a scanner of a 3D N×N×N image of an object volume without image reconstruction;
    converting without image reconstruction the volumetric sensor 3D dataset into a radon space representation having radon coordinate dimensions of distance and angle Θ and axial plane position;
    slicing the radon space representation without image reconstruction to produce a stack of two-dimensional (2D) images expressed by radon space and axial plane dimensions; and,
    playing back the stack of 2D images in a movie player to provide a rotating view of the 3D object volume without a computational expense and image quality degradation resulting from image reconstruction.

2. The method of claim 1, wherein acquiring a 3D dataset from scanner of a 3D object volume, comprises acquiring a 3D dataset from a tomographic scanner of a 3D object volume.

3. The method of claim 1, wherein acquiring a 3D dataset from a scanner of a 3D object volume, comprises acquiring a 3D dataset from a computed axial tomographic (CT) scanner of a 3D object volume.

4. The method of claim 1, wherein acquiring a 3D dataset from a scanner of a 3D object volume, comprises acquiring a 3D dataset from an x-ray scanner of a 3D object volume.

5. The method of claim 1, wherein acquiring a 3D dataset from a scanner of a 3D object volume, comprises acquiring a 3D dataset from a positron emission tomography (PET) scanner of a 3D object volume.

6. The method of claim 1, wherein acquiring a 3D dataset from an scanner of a 3D object volume, comprises acquiring a 3D dataset from tomography scanner selected from the group consisting of a Single Photon Emission Computed Tomography (SPECT), an Optical coherence tomography (OCT), an Electrical Impedance Tomography (EIT), an Electrical Resistivity Tomography (ERT), an Electrical Capacitance tomography (ECT), Cryo-electron Tomography (Cryo-ET), Magnetic Induction Tomography (MIT), Optical Projection Tomography (OPT), and Ultrasound assisted optical tomography (UAOT).

7. The method of claim 1, wherein acquiring a 3D dataset from an scanner of a 3D object volume, comprises acquiring a 3D dataset from a magnetic resonance imaging (MRI) scanner of a 3D object volume.

8. The method of claim 1, wherein acquiring a 3D dataset from an scanner of a 3D object volume, comprises acquiring a 3D dataset from ultrasound (US) scanner of a 3D object volume.

9. The method of claim 1, wherein slicing the converted dataset without image reconstruction to produce a sequence of two-dimensional (2D) projection images, comprises slicing the converted dataset along an angle (Θ) dimension of 3D radon coordinate space, to produce a sequence of 2D projection slices expressed in radon coordinate space dimensions of distance and axial plane position dimensions.

10. The method of claim 1, wherein slicing the converted dataset without image reconstruction to produce a sequence of two-dimensional (2D) projection images, comprises:
    applying N one-dimensional inverse Fourier transforms to transform the acquired 3D k-Space data into 3D Radon Space; and,
    slicing the 3D Radon Space along an angle (Θ) dimension of 3D Radon coordinate space, to produce a sequence of 2D projection slices expressed by the pair of 3D Radon coordinate space dimensions, being the distance and axial plane position dimensions.

11. The method of claim 1, wherein playing back the sequence of 2D images in a movie player to provide a rotating view of the 3D object volume, comprises playing back the sequence of 2D images in a movie player to provide a rotating view of the 3D object volume as a preview to a medical imaging scan prior to reconstructing the 3D image.

12. An imaging data processing system comprising:
    a scanner;
    a data acquisition module coupled to the scanner and configured to acquire three-dimensional (3D) volumetric sensor data of an N×N×N image of an object volume from the scanner without image reconstruction;
    data conversion logic coupled to the data acquisition module, the logic comprising program code enabled to convert without image reconstruction the acquired volumetric sensor 3D dataset into a Radon space representation having radon coordinate dimensions of distance and angle Θ and axial plane position, to slice the Radon space representation without image reconstruction along the Θ dimension to produce a stack of dimensional (2D) images expressed by Radon space and axial plane position dimensions; and,
    movie player configured to play back the stack of 2D images as a rotating view of the object volume without a computational expense and image quality degradation resulting from image reconstruction.

13. The system of claim 12, wherein the scanner is a tomographic scanner.

14. The system of claim 12, wherein the scanner is a magnetic resonance imaging (MRI) scanner.

15. The system of claim 12, wherein the object volume is one of a package or luggage.

16. A computer program product comprising a computer usable storage memory device storing computer usable program code for fast three-dimensional (3D) visualization of object volumes without image reconstruction, the computer program product comprising:
- computer usable program code for acquiring a volumetric sensor 3D dataset from a scanner of a 3D N×N×N image of an object volume without image reconstruction;
- computer usable program code for converting without image reconstruction the volumetric sensor 3D dataset into a radon space representation having radon coordinate dimensions of distance and angle Θ and axial plane position;
- computer usable program code for slicing the radon space representation without image reconstruction to produce a stack of two-dimensional (2D) images expressed by radon space and axial plane dimensions; and,
- computer usable program code for playing back the stack of 2D images in a movie player to provide a rotating view of the 3D object volume without a computational expense and image quality degradation resulting from image reconstruction.

17. The computer program product of claim 16, wherein the computer usable program code for acquiring a 3D dataset from an scanner of a 3D object volume, comprises computer usable program code for acquiring a 3D dataset from a tomographic scanner of a 3D object volume.

18. The computer program product of claim 16, wherein the computer usable program code for acquiring a 3D dataset from an scanner of a 3D object volume, comprises computer usable program code for acquiring a 3D dataset from a computed axial tomographic (CT) scanner of a 3D object volume.

19. The computer program product of claim 16, wherein the computer usable program code for acquiring a 3D dataset from an scanner of a 3D object volume, comprises computer usable program code for acquiring a 3D dataset from an x-ray scanner of a 3D object volume.

20. The computer program product of claim 16, wherein the computer usable program code for acquiring a 3D dataset from an scanner of a 3D object volume, comprises computer usable program code for acquiring a 3D dataset from a positron emission tomography (PET) scanner of a 3D object volume.

21. The computer program product of claim 16, wherein computer usable program code for acquiring a 3D dataset from an scanner of a 3D object volume, comprises computer usable program code for acquiring a 3D dataset from tomography scanner selected from the group consisting of a Single Photon Emission Computed Tomography (SPECT), an Optical coherence tomography (OCT), an Electrical Impedance Tomography (EIT), an Electrical Resistivity Tomography (ERT), an Electrical Capacitance tomography (ECT), Cryo-electron Tomography (Cryo-ET), Magnetic Induction Tomography (MIT), Optical Projection Tomography (OPT), and Ultrasound assisted optical tomography (UAOT).

22. The computer program product of claim 16, wherein the computer usable program code for acquiring a 3D dataset from an scanner of a 3D object volume, comprises computer usable program code for acquiring a 3D dataset from a magnetic resonance imaging (MRI) scanner of a 3D object volume.

23. The computer program product of claim 16, wherein the computer usable program code for acquiring a 3D dataset from an scanner of a 3D object volume, comprises computer usable program code for acquiring a 3D dataset from ultrasound (US) scanner of a 3D object volume.

24. The computer program product of claim 16, wherein the computer usable program code for slicing the converted dataset without image reconstruction to produce a sequence of two-dimensional (2D) projection images, comprises computer usable program code for slicing the converted dataset along an angle (Θ) dimension of 3D radon coordinate space, to produce a sequence of 2D projection slices expressed in radon coordinate space dimensions of distance and axial plane position dimensions.

25. The computer program product of claim 16, wherein the computer usable program code for slicing the converted dataset without image reconstruction to produce a sequence of two-dimensional (2D) projection images, comprises:
- computer usable program code for applying N one-dimensional inverse Fourier transforms to transform the acquired 3D k-Space data into 3D Radon Space; and,
- computer usable program code for slicing the 3D Radon Space along an angle (Θ) dimension of 3D Radon coordinate space, to produce a sequence of 2D projection slices expressed by the pair of 3D Radon coordinate space dimensions, being the distance and axial plane position dimensions.

26. The computer program product of claim 16, wherein the computer usable program code for playing back the sequence of 2D images in a movie player to provide a rotating view of the 3D object volume, comprises playing back the sequence of 2D images in a movie player to provide a rotating view of the 3D object volume as a preview to a medical imaging scan prior to reconstructing the 3D image.

* * * * *